United States Patent [19]
Clagett-Dame et al.

[11] Patent Number: 6,117,845
[45] Date of Patent: Sep. 12, 2000

[54] C-LINKED ANALOGS OF N-(4-HYDROXYPHENYL) RETINAMIDE

[75] Inventors: Margaret Clagett-Dame, Deerfield, Wis.; Robert W. Curley, Jr.; Kevin L. Weiss, both of Columbus, Ohio; Linda A. Tephly, Middleton; Vishal Sikri, Madison, both of Wis.

[73] Assignee: Ohio State University Research Foundation, Columbus, Ohio

[21] Appl. No.: 09/330,628

[22] Filed: Jun. 11, 1999

[51] Int. Cl.$^7$ .......................... A61K 31/70; A61K 31/07; C07H 15/00; C07C 35/18

[52] U.S. Cl. .............................. 514/35; 514/25; 514/725; 536/4.1; 568/824

[58] Field of Search ................ 536/4.1; 514/25, 514/725, 35; 568/824

[56] References Cited

U.S. PATENT DOCUMENTS

| | | | |
|---|---|---|---|
| 5,516,792 | 5/1996 | Curley, Jr. et al. | 514/459 |
| 5,574,177 | 11/1996 | Curley, Jr. et al. | 549/417 |
| 5,599,953 | 2/1997 | Curley, Jr. et al. | 549/417 |
| 5,663,377 | 9/1997 | Curley, Jr. et al. | 549/417 |
| 5,849,595 | 12/1998 | Alfano et al. | 436/16 |

FOREIGN PATENT DOCUMENTS

WO 96/13258  5/1996  WIPO.

OTHER PUBLICATIONS

Abou–Issa, H. M. et al. *Proc. Natl. Acad. Sci. USA* (1988) 85, 4181–4184.

Bhatnagar, R. et al. *Biochem. Pharmacol.* (1991) 41, 1471–1477.

Biesalski, H. K. *Toxicology* (1989 57, 177–161.

Clagett–Dame, M, JJ Repa (1997) "Methods for generating and characterizing retinoid receptors from *E. coli* and insect cell expression systems." *Methods in Enzymology—Vitamins and Coenzymes*, Part L, 282: 13–24.

Clagett–Dame, M, TJ Verhalen, JL Biedler, JJ Repa (1993) "Identification and characterization of all–trans–retinoic acid receptor transcripts and receptor protein in human neuroblastoma cells." *Arch Biochem Biophys* 300:684–693.

Curley, Jr. et al., Chemopreventice Activities of C–Glucoronide/Glycoside Analogs of Retinoid–O–Glucuronides Against Breast Cancer Development and Growth, *Anticancer Research* (1996), 16:757–764.

Hill, D. L. et al. *Ann. Rev. Nutrition* (1992) 12, 161–181.

Mehta, R. G. et al. *Oncology* (1991) 48, 1505–1509.

Moon et al. *Cancer Res.* (1979) 39, 1339–1346.

Newton et al. *Cancer Res.* (1980) 40, 3413–3425.

Rettig, WJ, BA Spengler, PG Chesa, LJ Old, JL Biedler (1987) Coordinate changes in neuronal phenotype and surface antigen expression in human neuroblastoma cell variants. *Cancer Res.* 47:1383–1389.

Sun et al, Retinoids as chemopreventive and therapeutic agents, *Drugs of the Future* (1998) (23)6:621–634.

Zile, M, HF DeLuca (1968) Retinoic acid: Some aspects of growth–promoting activity in the albino rat. *J. Nutr.* 94:302–308.

*Primary Examiner*—Elli Peselev
*Attorney, Agent, or Firm*—DeWitt Ross & Stevens SC

[57] ABSTRACT

Disclosed are acid-stable compounds of Formula I:

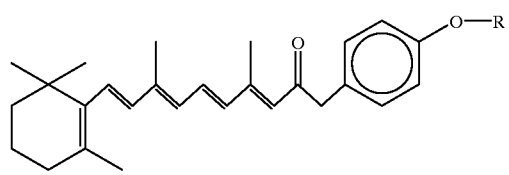

(I)

as well as pharmaceutical compositions containing the compounds as active ingredients, and methods to treat cancers in mammal, including humans, by administering one or more of the compounds to a subject in need thereof. The compounds are resistant to acid hydrolysis.

22 Claims, 3 Drawing Sheets

C-LINKED ANALOGS OF N-(4-HYDROXYPHENYL) RETINAMIDE

REFERENCE TO GOVERNMENT GRANT

This invention was made with United States government support awarded by the NIH, Grant #NIH CA49837. The United States has certain rights in this invention.

FIELD OF THE INVENTION

The invention is directed to 4-hydroxybenzylretinone and analogs thereof and the use of these compounds to treat cancer.

DESCRIPTION OF THE PRIOR ART

Breast cancer kills thousands of women annually. While surgical intervention has saved the lives of many women, radical and partial mastectomies often prove physically and emotionally debilitating. Indeed, surgery, even when combined with chemotherapy, may still expose the patient to the threat of possible recurrence.

A drug that promotes the prevention of breast cancer, as well as other cancers, is desirable, and massive research efforts have been directed to the development of such drugs. For example, retinoic acid, a vitamin A metabolite, and certain retinoic acid analogues, appear to be necessary for the maintenance of normal epithelial tissue differentiation and can reverse the metaplastic condition of hamster trachea in vitamin A deficient epithelial tissue. (Newton et al. Cancer Res. (1980) 40, 3413–3425). As a result, retinoic acid and certain amide analogues have been proposed as cancer chemopreventive agents, and display cancer preventive activity (Moon et al. Cancer Res. (1979) 39, 1339–1346). Similarly, retinoic acid analogues such as retinyl acetate, 13-cis-retinoic acid, and glucuronide analogues of retinoic acid also display cancer preventive activity, including breast cancer preventative activity (Hill, D. L. et al. Ann. Rev. Nutrition (1992) 12, 161–181 and Mehta, R. G. et al. Oncology (1991) 48, 1505–1509).

However, a major impediment to developing retinoic acid and its closely related analogues, has been their relatively high toxicity (Biesalski, H. K. Toxicology (1989) 57, 117–161). Side effects such as teratogenicity, hepatotoxicity, scaly skin, hair loss and headaches have been observed as a result of the use of most of these compounds. Researchers have been pursuing the synthesis of retinoic acid analogues with increased potency and/or reduced toxicity for application as cancer preventative agents. It has been found that N-(4-hydroxyphenyl) retinamide (hereinafter "4-HPR") displays chemopreventive activity in breast cancer (Moon et al. Cancer Res. (1979) 39, 1339–1346). Indeed, 4-HPR when combined with calcium glucarate, synergistically exerts an increased breast cancer chemopreventive activity in carcinogen-induced rat mammary tumors (Abou-Issa, H. M. et al.(1988) Proc. Natl. Acad. Sci. USA 85, 4181–4184). However, 4-HPR still displays teratogenic potential as evidenced by studies in the rat, mouse and the rabbit. See Kenel, M. F., Krayer, J. H., Merz, E. A. and Pritchard, J. R. (1988) "Teratogenicity of N-(4-hydroxyphenyl)-all-trans retinamide in rats and rabbits." Teratogenesis, Carcinogenesis and Mutagenesis 8:1–11; Kochhar, D. M. Shealy, Y. F., Penner, J. D. and Jiang, H. (1992) "Retinamides: hydrolytic conversion of retinoylglycine to retinoic acid in pregnant mice contributes to teratogenicity." Teratology 45:175–185. Furthermore, it impairs night vision in human patients (Kaiser-Kupter, M. I., Peck, G. K., Caruso, R. C., Jaffe, J D., DiGiovanna, J. J., Gross, E. G. (1986) "Abnormal retinal function associated with fenretinide, a synthetic retinoid." Arch Ophthalmol.104:69–70.; Costa, A., Malone, W., Perloff, M., Buranelli, F., Campa, T., Dossena, G., Magni, A., Pizzichetta, M., Andreoli, C., DelVecchio, M., Formelli, F., and Barbier, A. (1989) "Tolerability of the synthetic retinoid Fenretinide (HPR)." Eur. J. Cancer Clin. Oncol. 25:805–808).

There remains a long-felt need to have stable chemopreventive drugs for the prevention and treatment of various cancers, including breast cancer and neuroblastoma, which resist acid and enzymatic hydrolysis in vivo. It is this hydrolysis which may result in some of the side effects of existing compounds, whereas the positive chemotherapeutic/chemopreventive effects of the compound may reside in the intact molecule.

SUMMARY OF THE INVENTION

A first embodiment of the invention is drawn to compounds of Formula I:

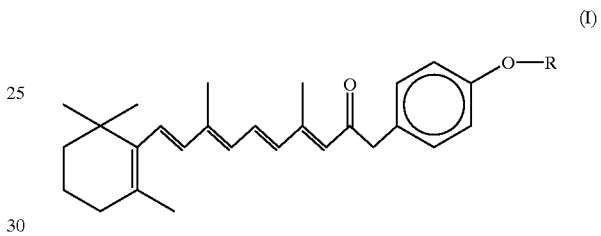

(I)

wherein R is selected from the group consisting of hydrogen,

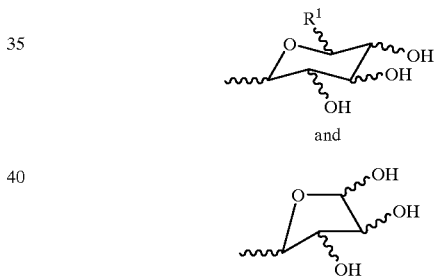

and wherein $R^1$ is selected from the group consisting of H, COOH, and $CH_2OH$; and salts thereof.

A second embodiment of the invention is directed to pharmaceutical compositions for preventing and/or treating cancer in humans. The compositions contain an effective cancer-preventing or cancer cell growth-inhibiting amount of one or more compounds of Formula I, optionally in combination with a pharmaceutically-suitable carrier therefor.

A third embodiment of the invention is directed to a method of preventing and/or treating cancer in mammals, including humans. The method comprises administering a cancer-preventive or cancer cell growth-inhibiting amount of a Formula I compound to a patient in need of such treatment.

The compounds of the present invention find utility in the treatment of cancer, especially breast cancer and neuroblastoma. Notably, the compounds exhibit marked antineoplastic activity and are useful to prevent and/or treat neoplastic growth in mammals. The compounds are also resistant to acid-catalyzed hydrolysis and are therefore quite stable in biological milieus.

DETAILED DESCRIPTION OF THE INVENTION

Abbreviations and Definitions

Figure 1:
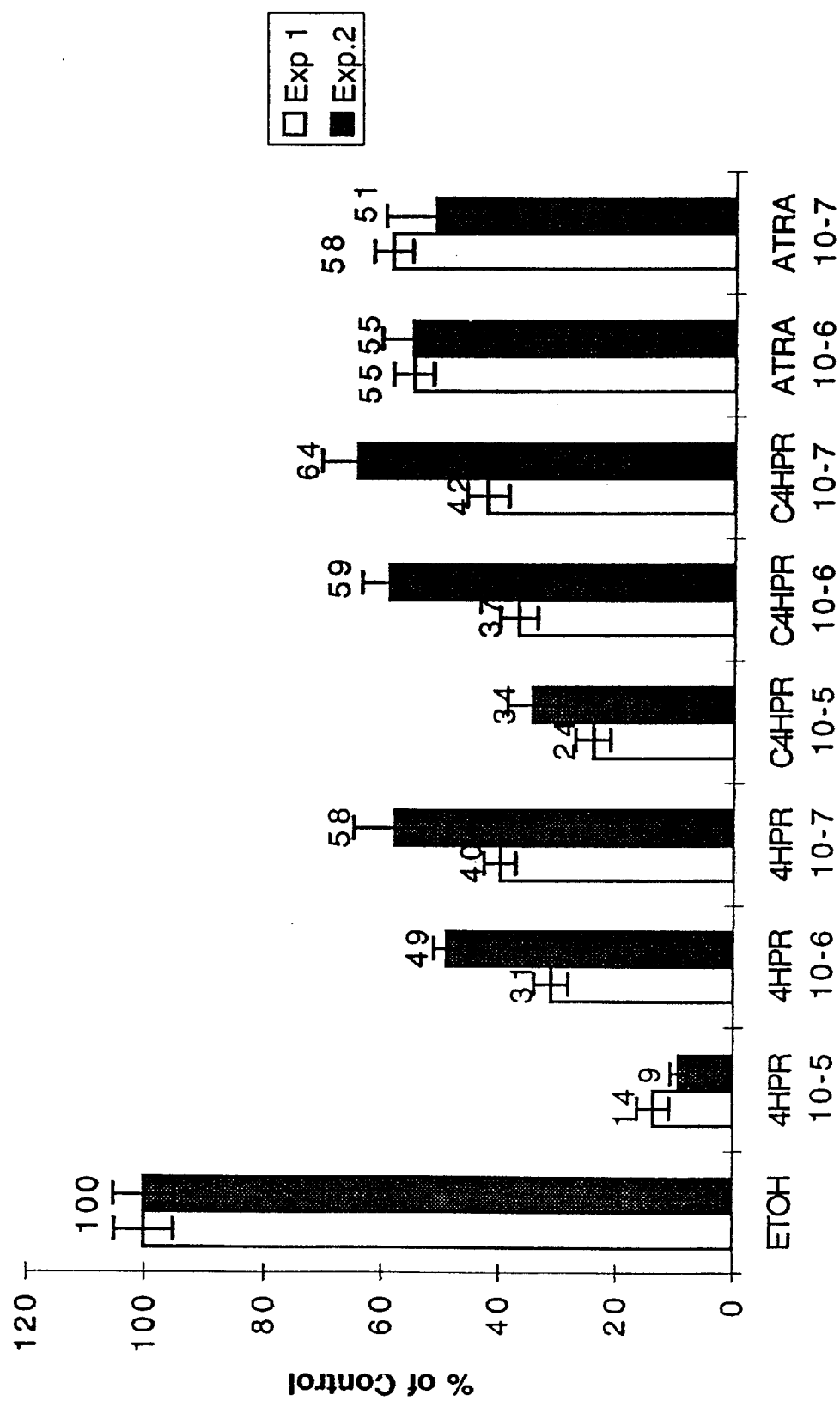
FIG. 1 is a graph depicting the viability of MCF7 cells after 72 hours of treatment with 4-HPR, 4-HBR (designated C4HPR in the figure), and all-trans retinoic acid (ATRA).

The following abbreviations are used throughout the specification and claims. Unless specifically defined to the contrary, all other terms have their standard accepted meanings. All of the following compounds can be purchased commercially from Aldrich Chemical Company, Milwaukee, Wis., USA, as well as other national and international suppliers:

"atRA"=all-trans retinoic acid
"CHAPS"=3-{(3-cholamidopropyl)-dimethylammonio}-1-propane-sulfonate
"DCE"=dichloroethane
"DCM"=dichloromethane
"DIA"=diisopropylamide
"EDTA"=ethylenediaminetetraacetic acid
"EtOAc"=ethyl acetate
"4-HBR"=4-hydroxybenzyl retinone
"4-HPR"=4-hydroxyphenyl retinamide
"LDA"=lithium diisopropyl amide
"PMSF"=phenylmethylsulfonyl fluoride
"RBP"=retinol-binding protein
"ROL"=all-trans retinol
"TBAF"=tetrabutylammonium fluoride
"TBS"=tert-butyldimethylsilyl
"TBSCl"=tert-butyldimethylsilyl chloride
"TFAA"=trifluoroacetic anhydride
"THF"=tetrahyrofuran
"TMS-CN"=trimethylsilyl cyanide
"TMS-OTf"=trimethylsilyl triflate (i.e., trimethylsilyl trifluoromethanesulfonate)

Chemistry

The compounds of the present invention are prepared by the synthetic procedures outlined in the following Reaction Schemes.

Intermediate products obtained may be quite suitable for use without further purification for the preparation of the final products, which then may be purified. Purification is readily achieved by conventional methods in the art, for example, by recrystallization techniques, chromatography, and the like.

The general procedure to synthesize the subject compounds begins by generating the benzyl portion of the compounds. This is done using Reaction Scheme 1 (preferred) to yield a 4-hydroxy (protected) benzyl bromide:

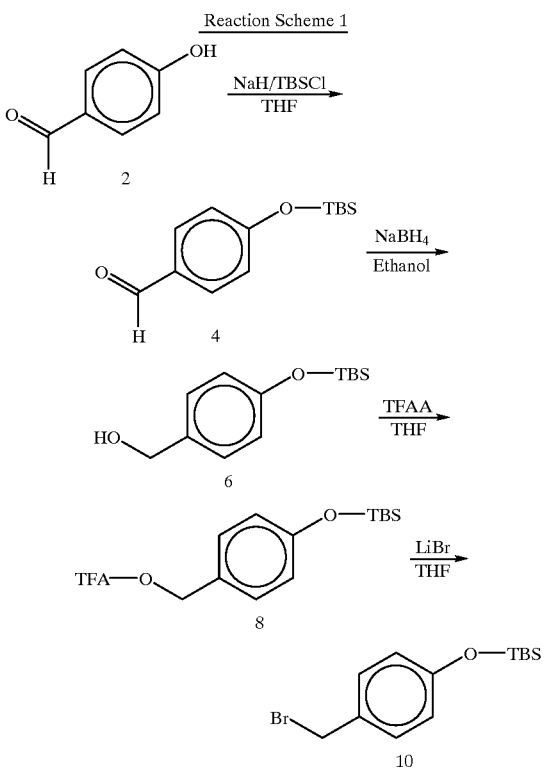

4-Hydroxybenzaldehyde 2 is treated with NaH and TBSCl in THF to yield 4-(TBS-oxy)benzaldehyde 4. Treating 4 with NaBH$_4$ in ethanol yields the protected alcohol 6. The alcohol 6 is then converted into the trifluoroacetate ester 8 by treating with TFAA in THF. The bromobenzyl derivative 10 is then afforded by treating 8 with LiBr. See the Examples for a detailed illustration.

The next step is to generate a protected analog of retinal which can be reacted with the benzyl bromide 10. In this case a protected cyanohydrin of retinal was used. To generate this intermediate, Reaction Scheme 2 is preferred:

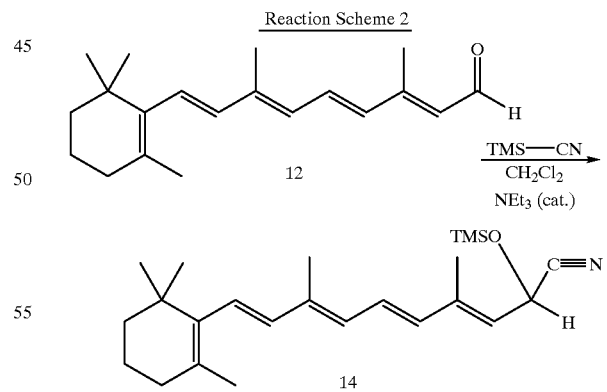

Here, retinal 12 (Sigma Chemical) is reacted with TMS-CN in the presence of triethyl amine to yield a TMS-protected cyanohydrin of retinal 14. In the protected cyanohydrin 14, the formerly aldehydic proton is now acidic due to the the presence of cyano group and can be reacted with the benzyl bromide 10 to yield the protected C-linked analog. See the Examples for a detailed illustration. Reaction Scheme 3 is preferred to accomplish this synthesis:

Reaction Scheme 3

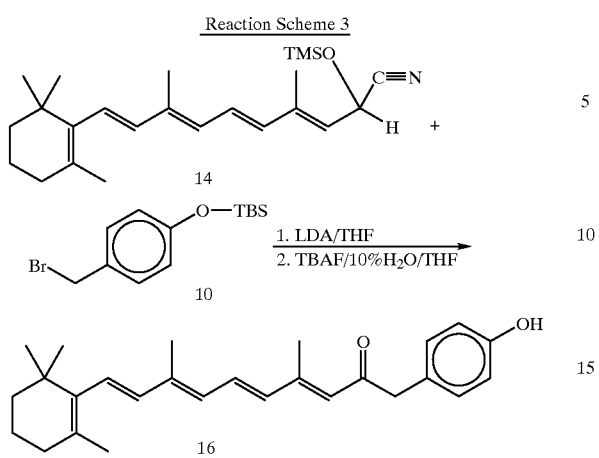

In Reaction Scheme 3, the protected retinal cyanohydrin 14 is reacted with the benzyl bromide 10 in the presence of LDA (generated in situ by adding DIA and n-butyl lithium). This yields an intermediate product, not shown, which is the C-linked analog of the product 16 which still retains the TBS protecting group on the phenolic oxygen and the TMS and cyano protecting groups masking the ketone oxygen. Treatment with TBAF removes both protecting groups, thereby causing the cyanohydrin group to react back to the ketone to yield the product, 4-HBR 16.

The 4-hydroxy benzyl derivative 16 can then be further reacted to append literally any manner of sugar moiety to the phenolic oxygen. The preferred route is shown in Reaction Schemes 4 and 5. Attaching a D-glucopyranosyl moiety to the phenolic oxygen of 16 is illustrated in these Reaction Schemes. Reaction Scheme 4 illustrates the generation of a suitably protected sugar molecule for reaction with 16 and Reaction Scheme 5 illustrates how the protected sugar molecule is attached to 16.

As shown in Reaction Scheme 4, methyl-1,2,3,4-tetra-O-acetylglucuronate 20 is prepared from glucurono-6,3-lactone 18 by first treating with base (NaOH) and then treating with acetic anhydride in pyridine. The mixture can be stored in the refrigerator. The resulting product is solid methyl-1,2,3,4-tetra-O-acetylglucuronate 20, which is filtered from the reaction solution and purified by recrystallization from ethanol.

Methyl 1-bromo-2,3,4-tri-O-acetylglucuronate 22 is prepared from 20 by treating 20 with 30% HBr/acetic acid overnight in the refrigerator. After removing the solvent under reduced pressure, the residue is dissolved in $CHCl_3$ and the $CHCl_3$ solution was washed with water, saturated $NaHCO_3$, saturated NaCl, and then dried over $Na_2SO_4$. The drying agent is removed by filtration and the residue recrystallized from ethanol to yield the bromo derivative 22.

The bromo derivative 22 is then dissolved in wet acetone with 1 equivalent of silver carbonate to remove the bromo group, thereby yielding the anomeric hydroxy intermediate 24. This intermediate can then be joined with compound 16 to yield compounds according to the invention, as shown in Reaction Scheme 5:

Reaction Scheme 5

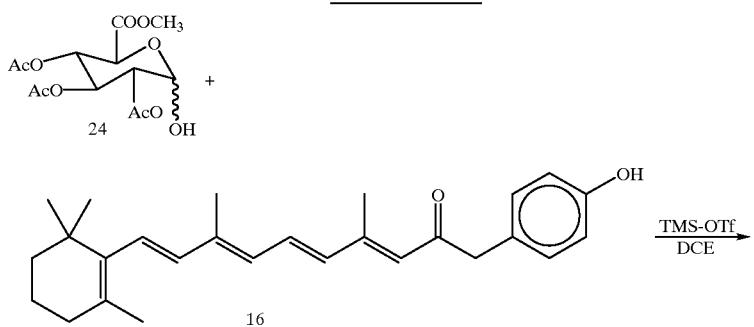

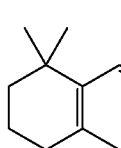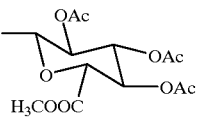

26

Here, 1 equivalent of the anomeric intermediate 24 and 1 equivalent of 4-HBR 16 are dissolved in DCE and TMS-OTf is added thereto. The reaction is allowed to proceed at room temperature with stirring overnight. This reaction yields 26. Compound 26 is then deprotected by saponifying the protecting groups. This is accomplished by dissolving 26 in a methanolic solution of potassium carbonate and allowing the reaction to proceed with stirring for 8 hours. In the same reaction vessel, 10% v/v of 6 N NaOH is added to hydrolyze the methyl ester. The solvent is removed under reduced pressure, the residue dissolved in acidic $CHCl_3$ and the $CHCl_3$ solution washed with water, saturated $NaHCO_3$, saturated NaCl, and then dried over $Na_2SO_4$. The drying agent is removed by filtration and the residue crystallized from ethanol to yield the deprotected product, 4-(retinonyl)-benzyloxyglucuronate.

Utility

The compounds find use in the treatment of cancer in mammals, including humans. This is shown using standard cell growth inhibition assays using various cancer cell lines. Presented here are cell growth inhibition studies using a human breast cancer cell line, MCF7, and a human neuroblastoma cell line, LA1–15n. Also presented is data showing the relative ability of the present compounds to compete with tritiated all-trans retinol for binding to retinol-binding protein.

Preparation of Compounds for Cell Culture and Binding Assays

All-trans retinoic acid (atRA) was purchased from Eastman Kodak, Rochester, N.Y. Stock solutions were prepared in 100% ethanol and concentrations were determined on a Shimadzu UV-2100 spectrophotometer (4-HBR: λmax=380 nm, ε=39,891; 4-HPR: λmax=365 nm, ε=47,900; atRA: λmax=340 nm, ε=45,300). Compound purity was assessed using a Waters HPLC-PDA with a 600E solvent delivery system using a Zorbax ODS, 250×4.6 mm, 5 micron column (Phenomenex, Torrance, Calif.). The column was equilibrated in 88% methanol/water with 10 mM ammonium acetate (flow rate of 1 ml/min). 4-HBR eluted at about 18 min., 4-HPR at about 12 min., and atRA at about 8 min with estimated purities of 96%, 100% and 100% respectively. Retinoids were blanketed with argon and stored at −70° C. until use.

Cell Culture

The clonal human neuroblastoma cell line LA1–15n was a kind gift from Dr. J. Biedler (Memorial Sloan Kettering Cancer Center, New York, N.Y.). The human mammary carcinoma cell line, MCF-7, was obtained from the American Type Culture Collection, 10801 University Boulevard, Manassas, Va. 20110-2209. Human neuroblastoma cells were maintained in a 1:1 mixture of Ham's F12:Eagle's MEM (Sigma, St. Louis, Mo.) medium supplemented with 3.376 g/L sodium bicarbonate and 10% heat-inactivated (30 min. at 57.5° C.) fetal calf serum (Hyclone, Logan Utah). MCF-7 cells were maintained in DMEM (Sigma) medium supplemented with 4 g/L glucose, 3.7 g/L sodium bicarbonate and 10% heat inactivated (60 min. at 60° C.) fetal calf serum. Medium was replaced every three days and cells were passed every 4–6 days.

Assay for Cell Growth Inhibition

Cells (100,000 cells) were passed into a 25 $cm^3$ flask in 10 ml of medium. After 24 hours, cells were dosed with 4-HPR, 4-HBR or atRA at concentrations of 0.1 μM, 1 μM or 10 μM. After 48 h, human neuroblastoma cells were resuspended by pipeting up and down and transferred to a 15 ml conical tube. After 72 h, 0.05% trypsin/0.02% EDTA was added to flasks containing MCF-7 cells followed by incubation for 2 min at 37° C. Cells were then removed from flasks and added to 8 ml of DMEM medium in a 15 ml conical tube to inactivate the trypsin. Cells were centrifuged at 1000 rpm for 10 min and resuspended in 2 ml of medium. Cells were triturated to obtain a uniform cell suspension and then 100 μl of the cell suspension was mixed with 100 μl of fluorescein diacetate (Molecular Probes; stock solution=0.1 g of fluorescein diacetate/1 ml of acetone; 1:10,000 in 0.9% saline=working solution). Two 20 μl aliquots were counted from each treatment group on a Nikon Diaphot 200 fluorescent microscope. Four out of five fields were counted on each side of the hemocytometer. Fluorescence was used to count the number of live cells and phase-contrast was used to count the number of total cells. The average number of live cells per field was divided by the total number of cells per field and expressed as a percentage of the control.

1. Growth Inhibition of MCF-7 Cells

The antiproliferative activity of 4-HPR, 4-HBR, and atRA against MCF-7 human mammary tumor cell culture models was determined using the above-described protocol. The results for MCF7 cells are shown in FIG. 1. In FIG. 1, 4HPR designates 4-hydroxyphenyl retinamide, C4HPR designates 4-hydroxybenzylretinone (16, i.e. 4-HBR), and ATRA designates all-trans retinoic acid. The experiment was repeated in duplicate. As is clearly shown in FIG. 1, compound 16 inhibits the growth of MCF7 cells in a dose-dependant fashion. The results of this experiment demonstrate the utility of the subject compounds to inhibit cancer cell growth.

2. Growth Inhibition of LA1–15n Cells

Figure 2:
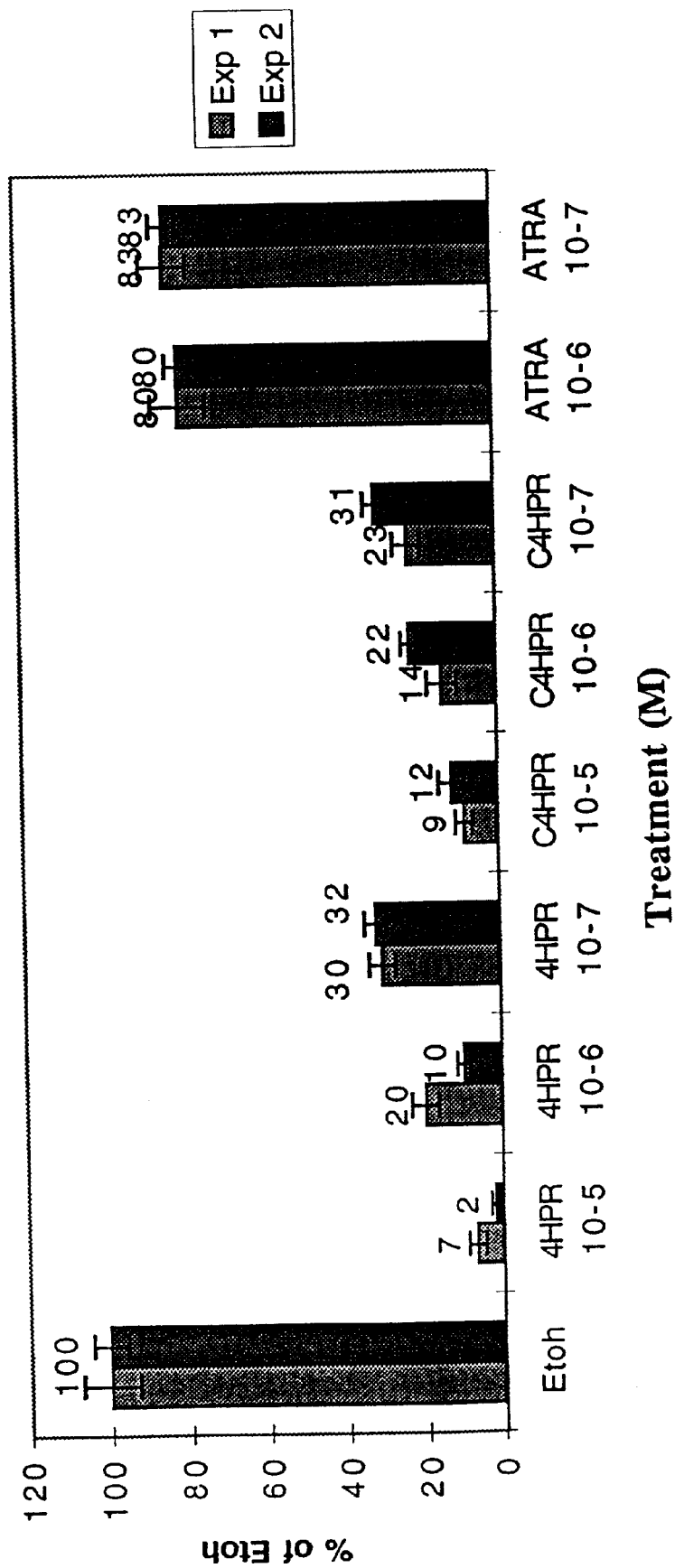
FIG. 2 is a graph depicting the viability of LA1–15n cells after 48 hours of treatment with 4-HPR, 4-HBR (designated C4HPR in the figure), and all-trans retinoic acid (ATRA).

Another experiment was performed which was similar to that described immediately above with the exception that the growth inhibition of cancer cell line LA1–15n was assayed and the test was 48 hours in duration. The assay was performed using the same protocol described hereinabove. The results are shown in FIG. 2 (the abbreviations are the same as in FIG. 1). The experiment was repeated in duplicate. As is clearly shown in FIG. 2, compound 16 (4-HBR) inhibits the growth of LA1–15n cells in a dose-dependant fashion. This results of this experiment further demonstrate the utility of the subject compounds to inhibit cancer cell growth.

3. Serum Retinol Binding Protein Binding Studies

RBP (human) was obtained commercially (Sigma). RBP (0.1 μg/μl) was incubated with 250 nM all-trans-($^3$H)-ROL (approx. 5 Ci/mmole) with and without competing ligands at 4° C. for 3 hours. Tritiated retinoid-labeled protein-containing extracts were treated with dextran-coated charcoal to remove unbound ligand before subjecting samples to sedimentation analysis on 5 to 20% sucrose density gradients. $^{14}$C-Labeled proteins were included with samples as internal sedimentation standards. Gradients were centrifuged at 257,000 g for 20 hours at 4° C. followed by fractionation and analysis of radioactivity. The results are shown in FIG. 3.

Figure 3:
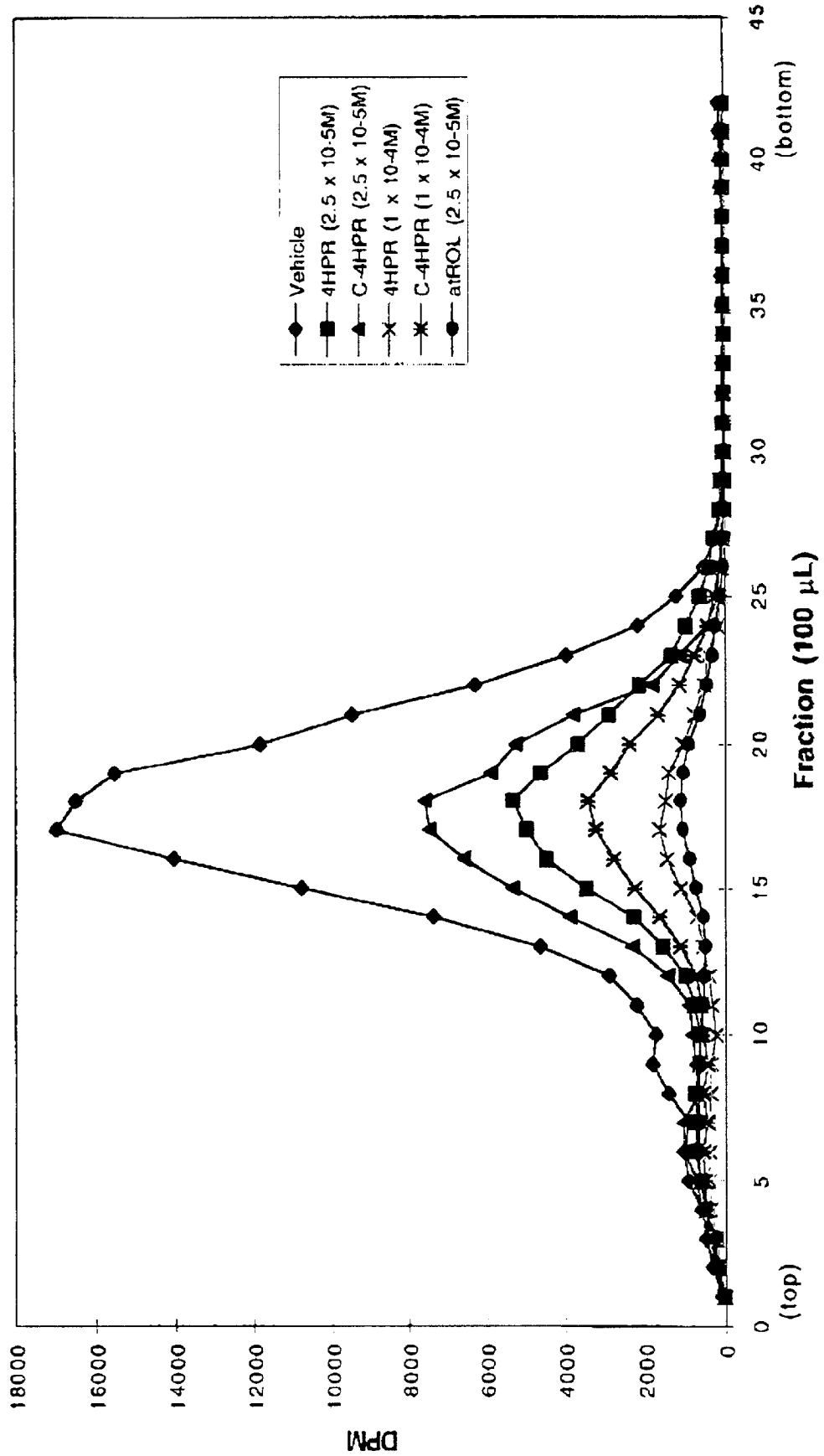
FIG. 3 is a graph depicting the affinity of 4-HPR, 4-HBR (designated C-HRP in the figure), and all-trans retinol (atrol) for serum retinol-binding protein.

As shown in FIG. 3, 4-HBR (designated C-4HPR in the figure) binds to serum RBP with less affinity than does 4-HPR. This is important because a troublesome side effect of 4-HPR is night blindness. This results because 4-HPR competes with the natural circulating form of all-trans retinol (Vitamin A) for binding to serum RBP. In contrast, 4-HBR does not have as great an affinity for serum RBP and therefore will be less likely to exhibit this side effect.

4. Acid Stability of 4-HBR

To demonstrate the stability of the 4-HBR under acidic conditions, a sample of 4-HBR was treated with 0.1 N methanolic HCl at 37° C. for 2 hours. After this time, the 4-HBR remained intact. Thus, this experiment shows that the subject compounds resist acid hydrolysis and will withstand the low pH of the mammalian stomach.

Pharmaceutical Compositions

Another aspect of the invention provides pharmaceutical compositions, for medical use, comprising an active compound, i.e., a Formula I compound or a pharmaceutically-acceptable salt therefor, in combination with an acceptable carrier therefor and optionally with other therapeutically-active ingredients or inactive accessory ingredients. The carrier must be pharmaceutically-acceptable in the sense of being compatible with the other ingredients of the formulation and not deleterious to the recipient. The pharmaceutical compositions include those suitable for oral, topical, inhalation, rectal or parenteral (including subcutaneous, intramuscular and intravenous) administration.

The formulations may conveniently be presented in unit dosage form and may be prepared by any of the methods well known in the art of pharmacy. The term "unit dosage" or "unit dose" is denoted to mean a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form.

Formulations of the present invention suitable for oral administration may be presented as discrete units such as capsules, cachets, tablets, boluses or lozenges, each containing a predetermined amount of the active compound; as a powder or granules; or in liquid form, e.g., as an aqueous solution, suspension, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine a mixture of the powdered active compound with any suitable carrier.

Formulations suitable for parenteral administration conveniently comprise a sterile preparation of the active compound in, for example, water for injection, saline, a polyethylene glycol solution and the like, which is preferably isotonic with the blood of the recipient.

Useful formulations also comprise concentrated solutions or solids containing the compound of Formula I which upon dilution with an appropriate solvent give a solution suitable for parenteral administration.

Preparations for topical or local applications comprise aerosol sprays, lotions, gels, ointments, suppositories etc., and pharmaceutically-acceptable vehicles therefore such as water, saline, lower aliphatic alcohols, polyglycerols such as glycerol, polyethylene glycerol, esters of fatty acids, oils and fats, silicones, and other conventional topical carriers. In topical formulations, the subject compounds are preferably utilized at a concentration of from about 0.1% to 5.0% by weight.

Compositions suitable for rectal administration, comprise a suppository, preferably bullet-shaped, containing the active ingredient and pharmaceutically-acceptable vehicles therefor such as hard fat, hydrogenated cocoglyceride, polyethylene glycol and the like. In suppository formulations, the subject compounds are preferably utilized at concentrations of from about 0.1% to 10% by weight.

Compositions suitable for rectal administration may also comprise a rectal enema unit containing the active ingredient and pharmaceutically-acceptable vehicles therefore such as 50% aqueous ethanol or an aqueous salt solution which is physiologically compatible with the rectum or colon. The rectal enema unit consists of an applicator tip protected by an inert cover, preferably comprised of polyethylene, lubricated with a lubricant such as white petrolatum and preferably protected by a one-way valve to prevent back-flow of the dispensed formula, and of sufficient length, preferably two inches, to be inserted into the colon via the anus. In rectal formulations, the subject compounds are preferably utilized at concentrations of from about 5.0–10% by weight. Useful formulations also comprise concentrated solutions or solids containing the active ingredient which upon dilution with an appropriate solvent, preferably saline, give a solution suitable for rectal administration. The rectal compositions include aqueous and non-aqueous formulations which may contain conventional adjuvants such as buffers, bacteriostats, sugars, thickening agents and the like. The compositions may be presented in rectal single dose or multi-dose containers, for example, rectal enema units.

Preparations for topical or local surgical applications for treating a wound comprise dressings suitable for wound care. In both topical or local surgical applications, the sterile preparations of compounds of Formula I are preferably utilized at concentrations of from about 0.1% to 5.0% by weight applied to a dressing.

Compositions suitable for administration by inhalation include formulations wherein the active ingredient is a solid or liquid admixed in a micronized powder having a particle size in the range of about 5 microns or less to about 500 microns or liquid formulations in a suitable diluent. These formulations are designed for rapid inhalation through the oral passage from conventional delivery systems such as inhalers, metered-dose inhalers, nebulizers, and the like. Suitable liquid nasal compositions include conventional nasal sprays, nasal drops and the like, of aqueous solutions of the active ingredient(s).

In addition to the aforementioned ingredients, the formulations of this invention may further include one or more optional accessory ingredient(s) utilized in the art of pharmaceutical formulations, i.e., diluents, buffers, flavoring agents, colorants, binders, surface active agents, thickeners, lubricants, suspending agents, preservatives (including antioxidants) and the like.

The amount of compound of Formula I required to be effective for any indicated condition will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. In general, a suitable effective dose is in the range of about 0.1 to about 500 mg/kg body weight per day, preferably in the range of about 5 to about 350 mg/kg per day, calculated as the non-salt form of Formula I. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

In general, the pharmaceutical compositions of this invention contain from about 0.5 mg to about 1.5 g active ingredient per unit dose and, preferably, from about 7.5 to about 1000 mg per unit dose. If discrete multiple doses are indicated, treatment might typically be 100 mg of a compound of Formula I given from two to four times per day.

The compounds according to the present invention may be administered prophylactically, chronically, or acutely. For example, such compounds may be administered prophylactically to inhibit the formation of cancers in the subject being treated. The subject compounds may also be administered prophylactically to patients suffering a primary cancer to prevent the occurrence of metastatic cancers. In addition to the prevention of primary and metastatic cancers, chronic administration of the subject compounds will typically be indicated in treating recurring cancers. Acute administration of the subject compounds is indicated to treat, for example, aggressive cancers prior to surgical or radiological intervention.

EXAMPLES

The following Examples are included solely to provide a more complete understanding of the present invention. The Examples do not limit the scope of the invention disclosed and claimed herein in any fashion.

4-{(t-Butyldimethylsilyl)oxy}benzaldehyde (4): To a dry 100 ml round bottom flask was added 1.31 g of 2. To this was added 50 ml of dry THF, followed by the careful addition of 298 mg NaH ($H_2$ is evolved). After evolution of hydrogen ceased, 1.93 g of TBSCl was added. The reaction was allowed to stir overnight. The solution was then diluted with 100 ml EtOAc, and washed sequentially with water and then brine. The organic layer was then dried with $MgSO_4$ and the solvent removed by evaporation. NMR on the crude product corresponded with the protected aldehyde 4.

4-{(t-Butyldimethylsilyl)oxy}benzyl alcohol (6): To a dry 250 ml round bottom flask was added 2.5 mg of 4, to which was added 100 ml of ethanol. $NaBH_4$ (794 mg) was slowly added thereto and the reaction stirred for 30 minutes. $NH_4Cl$ (sat'd solution) was carefully added to the reaction to quench excess $NaBH_4$, and the reaction then diluted with 125 ml water. The mixture was extracted with ether and the organic layers combined and washed with brine. The organic layers were again collected and the solvent removed in vacuo to yield the product 6.

4-{(t-Butyldimethylsilyl)oxy}benzyl trifluoroacetate (8): The benzyl alcohol 6 (12.9 g) was dissolved in dry THF; TFAA (13.6 g) was added with stirring, and the mixture refluxed for 30 minutes. After cooling to room temperature, the mixture was diluted with ether and washed three times with saturated $NaHCO_3$. The ether layer was dried, filtered, and concentrated. The product was obtained as a clear yellow oil in 98% yield.

4-{(t-Butyldimethylsilyl)oxy}benzyl bromide (10): The benzyl trifluoroacetate 8 (17.9 g) was dissolved in dry THF, and dry lithium bromide (5.06 g) was added with stirring. The mixture was refluxed overnight, cooled, diluted with acetonitrile, and extracted three times with hexane. The hexane layers were combined, dried, filtered, and concentrated, thereby leaving the product 10 as a white oil in 88% yield.

TMS-Protected retinal cyanohydrin (14): To retinal 12 (71.1 mg) in 1.5 ml DCM was added TMS-CN (29.8 mg) and 2.53 mg triethylamine. The reaction was stirred at room temperature and monitored by TLC using 90% hexanes/10% EtOAc as a solvent system. After 2 hours, the solvent was removed by heating gently in a water bath and bubbling argon through the reaction solution. The residue was again taken up in DCM and the solvent removed by rotary evaporation. NMR of the resulting residue showed it to be the TMS-protected cyanohydrin product 14 in essentially quantitative yield (99.7%).

4-hydroxybenzyl retinone (16): The cyanohydrin 14 (1.203 g) was combined with triethylamine (4.71 mg), DIA (0.471 g) and n-butyl lithium (1.86 ml of a 2.5 mmol solution). The reaction was stirred at −78° C. for 30 minutes and the protected benzyl bromide 10 (1.4 g) added via cannula. After dropwise addition of the benzyl bromide, the reaction was allowed to warm to room temperature over 3 hours. 1 equivalent of TBAF in 10% $H_2O$ in THF was added to deprotect the ketone and the phenol, thereby yielding the product 16.

Methyl-1,2,3,4-tetra-O-acetylglucuronate (20): Glucurono-6,3-lactone 18 (40 g) was dissolved in 300 ml of $CH_3OH$ containing 100 mg NaOH and allowed to stand one hour. The solvent was removed under reduced pressure and the residue dissolved in 100 ml pyridine and 150 ml acetic anhydride; the mixture was stored in the refrigerator. The resulting solid methyl-1,2,3,4-tetra-O-acetylglucuronate 20 was filtered and recrystallized from 95% ethanol. Compound 20 has a melting point of 178° C.

Methyl 1-bromo-2,3,4-tetra-O-acetylglucuronate (22): Compound 20 (50 g) was dissolved in 200 ml of 30% HBr/acetic acid; the mixture was allowed to stand overnight in the refrigerator. The solvent was removed under reduced pressure, the residue was dissolved in $CHCl_3$ and the $CHCl_3$ solution was washed with water, saturated $NaHCO_3$, saturated NaCl, and then dried over $Na_2SO_4$. The drying agent was removed by filtration and the residue crystallized from ethanol. The bromo derivative 22 has a melting point of 107° C.

Methyl 1-hydroxy-2,3,4-tri-O-acetylglucuronate (24): The bromo derivative 22 (1 eq.) was dissolved in wet acetone with 1 equivalent of silver carbonate to remove the bromo group, to yield 24 quantitatively.

4-(Retinonyl)benzyloxyglucuronate: The intermediate 24 (1 eq.) and 4-HBR 16 (1 eq.) were dissolved in DCE and excess TMS-OTf added thereto. The reaction was run overnight at room temperature with stirring, thereby yielding the protected product 26. Compound 26 was deprotected by dissolving in a solution of potassium carbonate in methanol and allowing the reaction to proceed with stirring for 8 hours. Into the same reaction vessel was then added 10% v/v of 6 N NaOH. The solvent was removed under reduced pressure, the residue dissolved in acidic CHCl₃ and the CHCl₃ solution washed with water, saturated NaHCO₃, saturated NaCl, and then dried over Na₂SO₄. The drying agent was removed by filtration and the residue crystallized from ethanol to yield the deprotected product, 4-(retinonyl) benzyloxyglucuronate.

The invention is not limited to the particular reagents, protocols, etc. described hereinabove, but includes all modified and equivalent forms thereof which are within the scope of the following claims.

What is claimed is:

1. A compound of Formula 1:

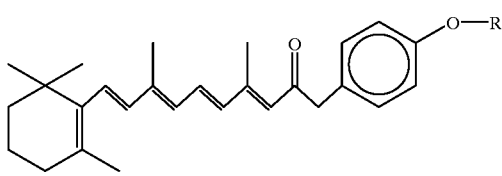

(I)

wherein R is selected from the group consisting of hydrogen,

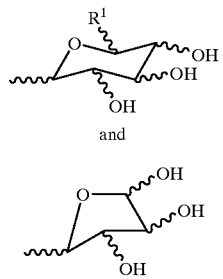

and wherein R¹ is selected from the group consisting of H, COOH, and CH₂OH; or a salt thereof.

2. The compound of claim 1, wherein R is hydrogen.
3. The compound of claim 1 wherein R is

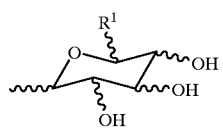

4. The compound of claim 3 wherein R¹ is H.
5. The compound of claim 3 wherein R¹ is COOH.
6. The compound of claim 3, wherein R¹ is CH₂OH.
7. The compound of claim 1, wherein R is

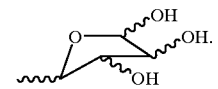

8. A pharmaceutical composition for treating cancer in mammals, the composition comprising an effective cancer cell growth-inhibiting amount of a compound according to claim 1 optionally in combination with a pharmaceutically-suitable carrier.

9. The composition of claim 8 comprising the compound wherein R is hydrogen.
10. The composition of claim 8 comprising the compound wherein R is

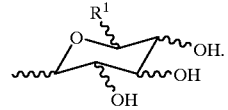

11. The composition of claim 10 comprising the compound wherein R¹ is H.
12. The composition of claim 10 comprising the compound wherein R¹ is COOH.
13. The composition of claim 10 comprising the compound wherein R¹ is CH₂OH.
14. The composition of claim 11 comprising a compound according to claim 1 wherein R is

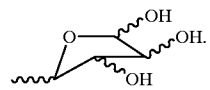

15. A method of treating cancer in mammals, the method comprising administering a cancer cell growth-inhibiting amount of a compound according to claim 1 to a patient in need thereof.
16. The method of claim 15 wherein a compound according to claim 1 wherein R is hydrogen is administered to the patient.
17. The method of claim 15 wherein a compound according to claim 1 wherein R is

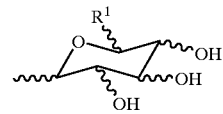

is administered to the patient.

18. The method of claim 17 wherein a compound wherein R¹ is H is administered to the patient.
19. The method of claim 17 wherein a compound wherein R¹ is COOH is administered to the patient.
20. The method of claim 17 wherein a compound wherein R¹ is CH₂OH is administered to the patient.
21. The method of claim 15 wherein a compound according to claim 1 wherein R is

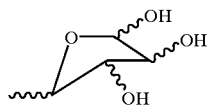

is administered to the patient.

22. The method of claim 15 wherein the patient in need thereof is a human patient.

* * * * *